(12) United States Patent
Frank et al.

(10) Patent No.: US 8,914,095 B2
(45) Date of Patent: Dec. 16, 2014

(54) METHOD FOR GENERATING A TRIGGER SIGNAL BY AN EKG SIGNAL AS WELL AS AN EKG MEASURING APPARATUS AND A MAGNETIC RESONANCE DEVICE

(75) Inventors: Michael Frank, Erlangen (DE); Jürgen Rössler, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 622 days.

(21) Appl. No.: 13/170,335

(22) Filed: Jun. 28, 2011

(65) Prior Publication Data

US 2012/0004569 A1    Jan. 5, 2012

(30) Foreign Application Priority Data

Jul. 2, 2010    (DE) .......................... 10 2010 025 920

(51) Int. Cl.
*A61B 5/05*    (2006.01)
*A61B 5/055*    (2006.01)
*A61B 5/0456*    (2006.01)
*A61B 5/00*    (2006.01)

(52) U.S. Cl.
CPC ............ *A61B 5/0456* (2013.01); *A61B 5/7239* (2013.01); *A61B 5/055* (2013.01)
USPC .......................................... 600/413; 600/509

(58) Field of Classification Search
CPC ............................ A61B 5/0006; A61B 5/0402
USPC ........................................................ 600/509
See application file for complete search history.

(56) References Cited

U.S. PATENT DOCUMENTS

| | | | |
|---|---|---|---|
| 2004/0073124 A1* | 4/2004 | Axel | 600/509 |
| 2006/0122490 A1* | 6/2006 | Sha et al. | 600/413 |
| 2006/0241392 A1* | 10/2006 | Feinstein et al. | 600/422 |
| 2007/0129915 A1* | 6/2007 | Blomberg et al. | 702/191 |
| 2008/0139926 A1* | 6/2008 | Frank et al. | 600/413 |

FOREIGN PATENT DOCUMENTS

| | | |
|---|---|---|
| DE | 102006058332 A1 | 6/2008 |
| DE | 102008023533 A1 | 11/2009 |
| DE | 102009015385 A1 | 9/2010 |

* cited by examiner

*Primary Examiner* — Christopher D Koharski
*Assistant Examiner* — Natasha Patel

(57) ABSTRACT

A method for generating a trigger signal for a magnetic resonance measurement by an R wave of an EKG signal is proposed. The EKG signal is captured by an algorithm manager. The algorithm manager includes at least a first trigger instance having a trigger algorithm. EKG signals from at least two different EKG channels are processed by the trigger algorithm. The algorithm manager includes at least a further trigger instance for capturing the EKG signal. The further trigger instance has at least one further trigger algorithm for processing EKG signals from at least two different EKG channels. The trigger signal is generated by selecting a trigger instance from the different trigger instances.

9 Claims, 3 Drawing Sheets

METHOD FOR GENERATING A TRIGGER SIGNAL BY AN EKG SIGNAL AS WELL AS AN EKG MEASURING APPARATUS AND A MAGNETIC RESONANCE DEVICE

CROSS REFERENCE TO RELATED APPLICATIONS

This application claims priority of German application No. 10 2010 025 920.9 filed Jul. 2, 2010, which is incorporated by reference herein in its entirety.

FIELD OF THE INVENTION

The present invention relates to a method for generating a trigger signal by an EKG signal, in particular an R wave of the EKG signal, an EKG measuring apparatus and a magnetic resonance device.

BACKGROUND OF THE INVENTION

EKG (electrocardiogram) measuring apparatuses are primarily used for measuring and monitoring the action of a patient's heart. To this end typically the summation voltage of the electrical activity of the myocardial fibers is measured as an "EKG signal" via at least two electrodes. FIG. 1 illustrates by way of example an ideal curve of such an EKG signal as a voltage U over time. Characteristic curves of the EKG signal are characterized in accordance with Einthoven by the letters P, Q, R, S and T and usually reproduce the different phases of a heartbeat.

In addition to simply monitoring the action of a patient's heart there are other applications. For example, EKG signals are also used in medical imaging for generating trigger signals. The EKG signal is used during imaging to obtain information about the cardiac phase, in order thus to synchronize the imaging with the activity of the heart. In particular in imaging methods that require a longer recording time, high-quality cardiac recordings or even recordings of regions that are moved by the heartbeat can be created.

EKG measuring apparatuses are also used during an examination of a patient by means of a magnetic resonance device, for example for in-situ recording of EKG signals. In this case however the operation in the magnetic resonance device places special demands on the EKG measuring apparatus because of the strong gradient fields and high-frequency fields used there for imaging, in order to prevent mutual interference between magnetic resonance device and EKG measuring apparatus. EKG measuring apparatuses that are magnetic-resonance-compatible in the aforementioned sense are available on the market.

The determination of R waves in EKG signals is essential for reliable triggering. However, this determination is made more difficult e.g. by T wave elevations occurring in the magnetic field. A further major ongoing problem for reliable EKG signal measurement is temporally changing magnetic fields, as are used in the magnetic resonance device as magnetic gradient fields for spatial encoding. Such temporally changing magnetic fields generate interference voltages according to the law of induction, which are coupled in as interference in the EKG signal recorded by the EKG electrodes. Such magnetically generated interference signals overlap with the EKG signal generated by the heart and distort it.

These interferences are highly undesirable. To synchronize a recording of a magnetic resonance image with the heartbeat it is necessary to reliably identify the R wave of the EKG signal. The interference signals can, e.g. because of their often similar shape, be erroneously interpreted as an R wave and thus incorrectly trigger a recording of a magnetic resonance image. On the other hand it can happen that a "genuine" R wave is not identified as such because of the overlaid interference signals. This regularly leads to a significant worsening of the image quality.

SUMMARY OF THE INVENTION

The object of the present invention is in particular to provide a method or an EKG measuring apparatus or a magnetic resonance device in which reliable detection of R waves of EKG signals measured in the magnetic resonance device is achieved. The object is achieved by the features of the independent claims. Advantageous embodiments are described in the dependent claims.

The invention is based on a method for generating a trigger signal by means of an EKG signal, in particular an R wave of the EKG signal, comprising at least one learning step, in which the EKG signal is captured by means of an algorithm manager with at least one first trigger instance which comprises at least one trigger algorithm by means of which signals from at least two different EKG channels can be processed.

It is proposed that in the learning step at least one further trigger instance for capturing the EKG signal is available to the algorithm manager, the further trigger instance comprising at least one trigger algorithm which processes signals from at least two different EKG channels. In this connection a trigger instance should be understood in particular as a decision-making level for a trigger decision for initiating and/or triggering and/or synchronizing a measurement, such as for example a magnetic resonance measurement, the two EKG signals from the two different EKG channels being received in this decision level. The algorithm manager preferably comprises a trigger algorithm for calculating a trigger event, in particular a detection of an R wave in the individual EKG signals, for the individual trigger instances. Preferably the trigger algorithm is designed such that the signals from two different EKG channels can be combined in one trigger instance. In principle however an alternative embodiment of the trigger algorithm is also conceivable. Thanks to the inventive embodiment a reliable, in particular an optimum, and robust detection of R waves of EKG signals measured and/or captured in the magnetic resonance device can be achieved, in that to this end multiple trigger instances are available for the detection. In this way a trigger signal for a magnetic resonance measurement can be very reliably generated. Furthermore low-cost trigger algorithms and/or trigger managers which in particular take into account and/or have only two signal inputs or channels for generating trigger signals can be used for generating trigger signals, although more than two channels, in particular EKG channels, can be employed for generating the trigger signal. Preferably the trigger instance that has an optimum detection of the R wave can be selected by the algorithm manager from the different trigger instances for generating the trigger signal.

It is furthermore proposed that the different trigger instances have the same value as one another. The different trigger instances can here be used for reliable detection of R waves in the individual EKG channels on the same trigger level.

Especially advantageously, signals from at least three EKG channels are processed in the different trigger instances. Different EKG channels can here be assigned to the different trigger instances and thus a large variation in a combination of at least two EKG channels for the individual trigger instances can be achieved. Advantageously at least one EKG channel of a first trigger instance is here different from at least one EKG channel of a further trigger instance.

It is further proposed that a maximum number k of trigger instances is specified by $k=(n*(n-1)/2)$, where n is formed by a maximum number of the EKG channels. A maximum number of trigger instances should here be understood in particular as a maximum number of possible combinations of for example two EKG channels in each case to form a trigger instance. Thus a maximum combination of the different EKG channels with one another for the different trigger instances can be achieved, so that significantly higher reliability and robustness for detection of the R wave of an EKG signal can be achieved. Preferably the above condition for the maximum number of trigger instances is satisfied if in each case two EKG channels are combined in one trigger instance. In principle it is conceivable that in the case of a trigger algorithm that is alternative to the present invention further conditions can be present for the maximum number of trigger instances.

In an advantageous development of the invention it is proposed that in a selection step one of the trigger instances is selected for a synchronization, in particular a magnetic resonance measurement. The criteria obtained in the learning process, in particular trigger criteria for a synchronization of a magnetic resonance measurement of the magnetic resonance device with the EKG signals, can be applied here. Particularly advantageously, the selection occurs here on the basis of an R wave shape of the EKG signal and/or on the basis of an energy value which is determined by means of a temporal derivation of the EKG signal. The R wave shape here preferably corresponds to an R wave shape prototype. The energy value is advantageously specified by a maximum energy of a pulse shape, the maximum energy being formed by means of a lowpass-filtered value of a temporal derivation of a magnitude, the magnitude being comprised of the root of the sum of the squared individual EKG signals used in the respective trigger instance.

In a further embodiment of the invention it is proposed that in a measurement step a trigger signal is generated by means of the selected trigger instance. Preferably the measurement step takes place subsequent to the selection step, so that the selection criteria reached in the selection step can be adapted for a subsequent synchronization for a subsequent magnetic resonance measurement using the magnetic resonance device.

Furthermore it can be provided for in the measurement step that the remaining trigger instances not selected in the selection step are deactivated. A fast signal capture can be achieved here, since a high computing power and/or a processor power of an arithmetic unit and/or of a processor unit can be made available for the selected trigger instance.

The invention is further based on an EKG measuring apparatus which comprises at least one trigger unit, an algorithm manager and at least two different trigger instances being implemented in the trigger unit for generating a trigger signal.

Furthermore the invention is based on a magnetic resonance device with an EKG measuring apparatus, which comprises at least one trigger unit, an algorithm manager and at least two different trigger instances being implemented in the trigger unit for generating a trigger signal.

BRIEF DESCRIPTION OF THE DRAWINGS

Further advantages, features and details of the invention emerge from the exemplary embodiment described in the following, as well as on the basis of the drawings, which show.

DETAILED DESCRIPTION OF THE INVENTION

On the basis of FIGS. 2 to 6 the inventive method is explained in greater detail in the following in conjunction with an EKG measuring apparatus 10 and a magnetic resonance device 1.

Figure 2:
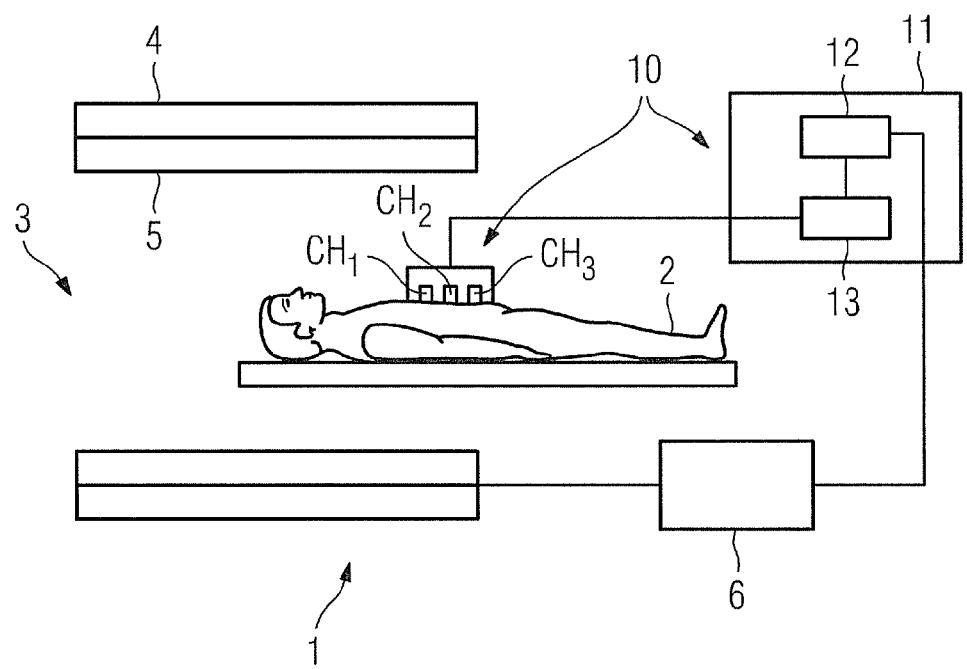
FIG. 2 an inventive magnetic resonance device with an inventive EKG measuring apparatus in a schematic illustration, FIG. 3 a schematic illustration of a sequence of an inventive method, FIG. 4 a schematic illustration of a learning step of the inventive method, FIG. 5 a schematic illustration of a selection step of the inventive method and FIG. 6 a schematic illustration of a measurement step of the inventive method.
Figure 3:
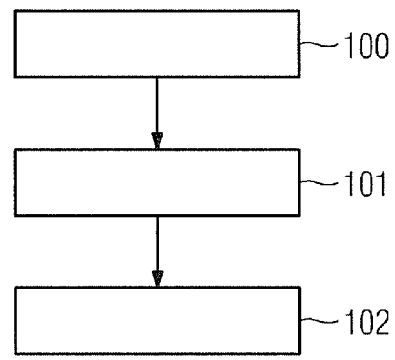
Figure 4:
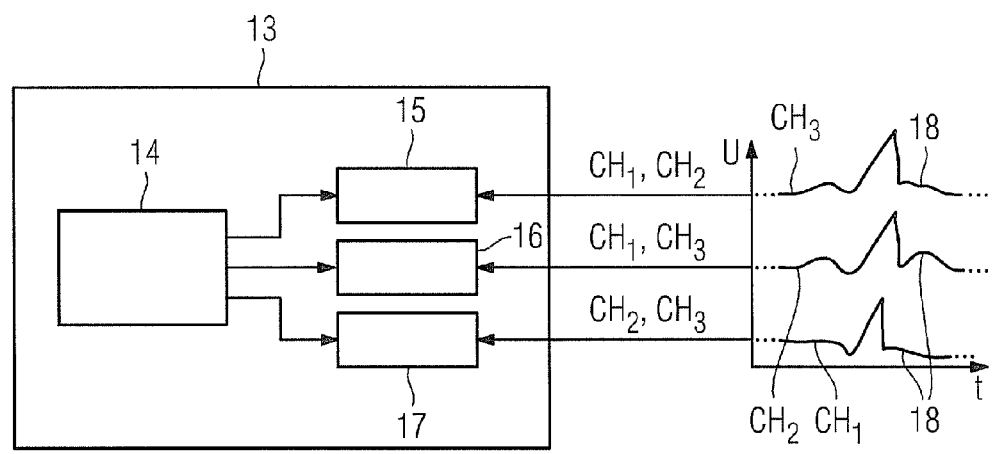

During an examination a patient 2 is located with an attached EKG measuring apparatus 10 in a recording region 3 of the magnetic resonance device 1 to record the patient 2, FIG. 2. The EKG measuring apparatus 10 is to this end designed to be magnetic-resonance-compatible. The magnetic resonance device 1 comprises a magnet unit 4 with a main magnet and a coil unit 5 with a gradient coil and a high-frequency coil. Control of the individual components of the magnetic resonance device 1 is effected via a control unit 6.

The magnetic resonance device 1 as well as the EKG measuring apparatus 10 are here illustrated only schematically, since the design in principle of the magnetic resonance device 1 as well as the design in principle of an EKG measuring apparatus 10 with EKG electrodes and amplifier/filter units for measuring a voltage between two EKG electrodes is known to the person skilled in the art.

According to the invention the magnetic resonance device 1 in particular comprises the EKG measuring apparatus 10, which has a processing unit 11 with an arithmetic unit 12 and a trigger unit 13. The separate or consolidated illustration of these units is not to be understood as absolutely physical, but rather as a separation or combination by coherent units. The EKG measuring apparatus 10, in particular the processing unit 11, the arithmetic unit 12 and the trigger unit 13, are connected to the magnetic resonance device 1 and to one another for the transmission of data.

The EKG measuring apparatus 10 is here advantageously shown as comprising three EKG channels CH1, CH2, CH3. The inventive method (FIG. 3 to 6) is described in the following on the basis of these three EKG channels CH1, CH2, CH3. However, in an alternative embodiment of the invention the method can also be performed with more than the three EKG channels CH1, CH2, CH3 described.

The trigger unit 11 comprises an algorithm manager 14 and three trigger instances 15, 16, 17, which in each case comprise a trigger algorithm. A maximum number k of the trigger instances 15, 16, 17 is specified here by $k=(n*(n-1)/2)$, where n is formed by a maximum number of the EKG channels CH1, CH2, CH3, here n=3. To this end the trigger unit 11 has computer programs (not shown in greater detail) and/or trigger electronics (not shown in greater detail) for triggering an EKG signal 18, in particular an R wave of the EKG signal 18. The individual trigger algorithms for the different trigger instances 15, 16, 17 can be implemented here by means of the algorithm manager 14 and/or by means of further units or means which seem expedient to the person skilled in the art.

The inventive method for generating a trigger signal by means of an EKG signal 18, in particular an R wave of the EKG signal 18, comprises a learning step 100, which takes place prior to a magnetic resonance measurement. In the learning step 100 the EKG signal 18 is captured by means of the algorithm manager 14, the algorithm manager 14 administering the multiple trigger instances 15, 16, 17 for this. The individual trigger instances 15, 16, 17 comprise a trigger algorithm, by means of which the signals from two different EKG channels CH1, CH2, CH3 in each case are captured and processed.

The learning step 100 generally takes place prior to a magnetic resonance measurement, for example during a phase in which the patient couch together with the patient 2 is still situated outside the magnet of the magnetic resonance device 1. A decision as to whether a learning step 100 is started is effected automatically by the algorithm manager 14. Moreover the learning step 100 or the inventive method can also be started manually by operating personnel.

During the learning step 100 (FIG. 4) each of the three trigger instances 15, 16, 17 is fed two of the three EKG channels CH1, CH2, CH3, the individual trigger instances 15, 16, 17 differing in at least one EKG channel CH1, CH2, CH3 from the further two trigger instances 15, 16, 17. Thus for example the EKG channels CH1, CH2 are fed to the first trigger instance 15, the EKG channels CH1, CH3 to the second trigger instance 16 and the EKG channels CH2, CH3 to the third trigger instance 17. The individual trigger algorithms of the individual trigger instances 15, 16, 17 differ in respect of processing and evaluating the different EKG channels CH1, CH2, CH3. Furthermore the different trigger instances 15, 16 and 17 are equal in value to one another, in that these different trigger instances 15, 16, 17 are arranged on the same trigger level.

By means of the different trigger instances 15, 16, 17 signals from different EKG channels CH1, CH2, CH3 are captured and within the different trigger instances 15, 16, 17 an R wave in the EKG signals 18 is captured. On the basis of the differently occupied inputs in the different trigger instances 15, 16, 17 with the different EKG channels CH1, CH2, CH3 three different trigger results are available to the algorithm manager 14 or the trigger unit 13 (FIG. 5).

Figure 1:
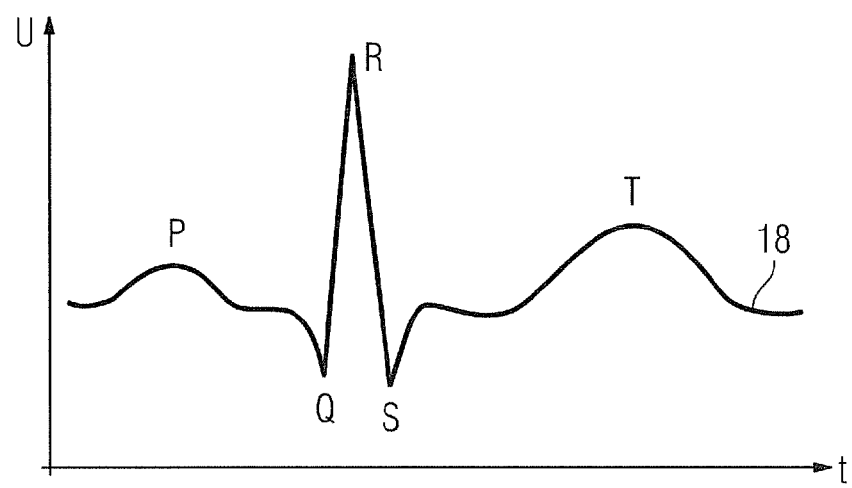
FIG. 1 an ideal curve of an EKG signal over a time.

To generate a trigger signal the R wave, in particular a prototype of the R wave, of the EKG signal 18 is initially captured in the learning step 100. This occurs simultaneously in all three trigger instances 15, 16, 17, the different EKG channels CH1, CH2, CH3 in each case forming the basis for capturing the R wave shape. During the learning step 100 an increase in the R wave of the EKG signal 18 between the Q wave and the R wave, in particular between a minimum of the Q wave and a maximum of the R wave, in FIG. 1, is captured as efficiently as possible in the individual trigger instances 15, 16, 17. Alternatively or additionally an energy value can be determined and/or captured from sampling values of the R wave shape in the learning step 100. The energy value of the corresponding pulse shape is here formed by a lowpass-filtered temporal derivation of a magnitude, the magnitude being comprised of the root of a sum of the squared individual EKG signal values of the individual EKG channels. Preferably in the learning step 100 the individual trigger algorithms try to detect the energy value directly prior to a maximum of the R wave. In the learning step 100 each of the three trigger instances 15, 16, 17 undergoes a learning phase independently of the other trigger instances 15, 16, 17 in each case to capture the R wave or an R wave prototype. However, in principle other decision-making criteria are also conceivable for detecting and/or capturing the R wave within the EKG signal 18 during the learning step 100.

Figure 5:
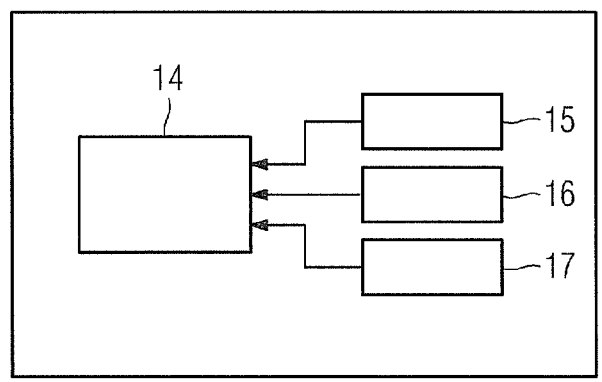

The learning step 100 is followed by a selection step 101, in which the trigger instance 15, 16, 17, by means of which a trigger signal for the magnetic resonance measurement is generated in a measurement step 102, is selected by the algorithm manager 14 (FIG. 5). To this end, initially the individual information and/or measurement results from the individual trigger instances 15, 16, 17 which were obtained in the learning step 100 are sent from said trigger instances 15, 16, 17 via a data transfer unit (not described in greater detail) to the algorithm manager 14. Here in each case an item of information as to whether an R wave prototype was captured is sent from the individual trigger instances 15, 16, 17 to the algorithm manager 14. Moreover, when an R wave prototype is captured and/or discovered in one of the trigger instances 15, 16, 17 the energy value of the corresponding pulse shape is further sent by the latter to the algorithm manager 14. Because the energy value of the R wave pulse shape is advantageously detected directly prior to the maximum of the R wave of the EKG signal 18, it is ensured that the selected trigger instance 15, 16, 17 has captured the R wave prototype that can be best detected in the corresponding combination of two of the three EKG channels CH1, CH2, CH3.

In the selection step 101 the trigger instance 15, 16, 17 that captured an R wave prototype is now selected by the algorithm manager 14 for generating trigger signals for a subsequent magnetic resonance measurement. If multiple trigger instances 15, 16, 17 have captured an R wave prototype, the energy value for the individual R wave prototype is added in the algorithm manager 14 as a further selection criterion for the individual trigger instances 15, 16, 17. The energy value is in this case determined by means of a temporal derivation of the respective EKG signal 18 for the individual EKG channels CH1, CH2, CH3. In this way offsets that would affect the energy value or a determination of the energy value are advantageously suppressed. Here the trigger instance 15, 16, 17 which besides capturing the R wave prototype moreover has the greatest energy value for this R wave prototype is selected by the algorithm manager 14.

Figure 6:
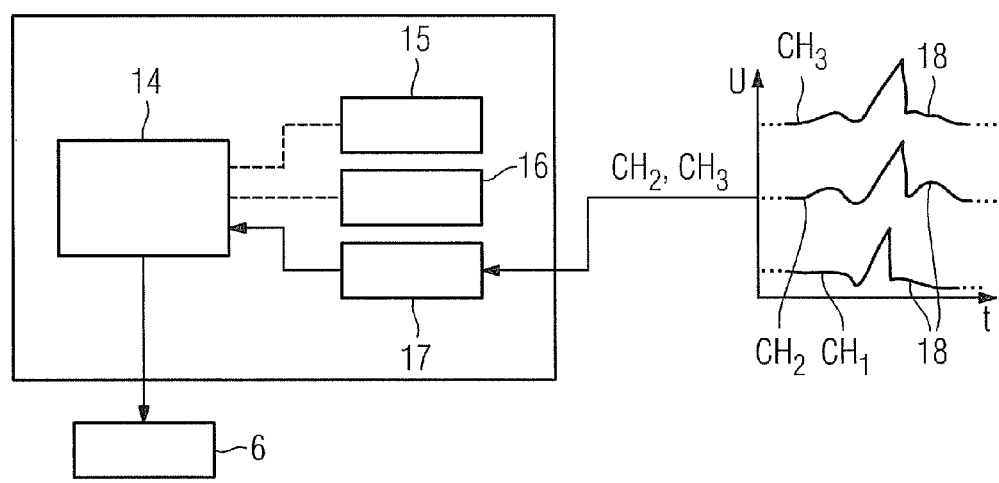

After the selection step 101 the measurement step 102 of the method is started. The trigger instance 15, 16 or 17 selected by the algorithm manager 14 is activated here to generate the trigger signal, while the other two trigger instances 15, 16 or 17 are deactivated. The activation or deactivation of the individual trigger instances 15, 16 or 17 is preferably effected here by means of the algorithm manager 14 (FIG. 6).

The trigger data captured by the selected trigger instance 15, 16 or 17 is forwarded in the measurement step 102 from the trigger instance 15, 16 or 17 to the algorithm manager 14 and is routed by the latter via the arithmetic unit 12 to the control unit 6 of the magnetic resonance device 1 for triggering or synchronization of the magnetic resonance measurement for a recording of a magnetic resonance image.

The inventive method is advantageously performed each time after the EKG measuring apparatus 10 is attached to the patient 2 prior to performing the magnetic resonance measurement which is planned with the magnetic resonance device 1 and which requires triggering.

The invention claimed is:
1. A method for generating a trigger signal for a magnetic resonance measurement by an EKG signal, comprising:
   capturing a plurality of EKG signals from a plurality of different EKG channels prior to the magnetic resonance measurement;

calculating a first trigger instance by processing a combination of at least two EKG signals captured from at least two EKG channels of the plurality of different EKG channels prior to the magnetic resonance measurement;

calculating a further trigger instance by processing a further combination of at least two EKG signals captured from at least two EKG channels of the plurality of different EKG channels prior to the magnetic resonance measurement, wherein one of the at least two EKG channel for calculating the first trigger instance is different from one of the at least two EKG channel for calculating the further trigger instance; and selecting the trigger signal from the first and the further trigger instances for triggering the magnetic resonance measurement to record a magnetic resonance image.

2. The method as claimed in claim 1, wherein the first trigger instance equals to the further trigger instance.

3. The method as claimed in claim 1, wherein EKG signals from at least three different EKG channels are processed at the first and the further trigger instances.

4. The method as claimed in claim 1, wherein a maximum number k of trigger instances is specified by:

$$k=(n*(n-1)/2),$$

where n is a maximum number of EKG channels.

5. The method as claimed in claim 1, wherein the selection is based on an R wave shape of the EKG signal.

6. The method as claimed in claim 1, wherein the selection is based on an energy value determined by a temporal derivation of the EKG signal.

7. The method as claimed in claim 1, wherein a trigger instance that is not selected from the first and the further trigger instances is deactivated.

8. An EKG measuring apparatus, comprises:
a plurality of different EKG channels for capturing a plurality of EKG signals prior to a magnetic resonance measurement;

an algorithm manager for calculating a first trigger instance by processing a combination of at least two an EKG signals captured from at least two EKG channels of the plurality of different EKG channels and calculating a further trigger instance by processing a further combination of at least two EKG signals captured from at least two EKG channels of the plurality of different EKG channels prior to the magnetic resonance measurement, wherein one of the at least two EKG channel for calculating the first trigger instance is different from one of the at least two EKG channel for calculating the further trigger instance; and a trigger unit for selecting a trigger signal from the first and the further trigger instances for triggering the magnetic resonance measurement to record a magnetic resonance image.

9. A magnetic resonance device, comprising:
an EKG measuring apparatus comprising:
a plurality of different EKG channels for capturing a plurality of EKG signals prior to a magnetic resonance measurement;

an algorithm manager for calculating a first trigger instance by processing a combination of at least two EKG signals captured from at least two EKG channels of the plurality of different EKG channels and calculating a further trigger instance by processing a further combination of at least two EKG signals captured from at least two EKG channels of the plurality of different EKG channels prior to the magnetic resonance measurement, wherein one of the at least two EKG channel for calculating the first trigger instance is different from one of the at least two EKG channel for calculating the further trigger instance; and a trigger unit for selecting a trigger signal from the first and the further trigger instances for triggering the magnetic resonance measurement to record a magnetic resonance image.

* * * * *